United States Patent [19]  [11] Patent Number: 4,937,201
Ueno et al.  [45] Date of Patent: Jun. 26, 1990

[54] LATEX REAGENT FOR DETECTION OF THE TOXIN OF *CLOSTRIDIUM DIFFICILE*

[75] Inventors: Kazue Ueno, Hidase 453, Seki, Gifu-ken; Hideki Kohno; Satoshi Tsutsui, both of Kanagawa, all of Japan

[73] Assignees: Mitsubishi Kasei Corporation, Tokyo; Kazue Ueno, Gifu, both of Japan

[21] Appl. No.: 495,487

[22] Filed: May 17, 1983

[30] Foreign Application Priority Data

Jun. 10, 1982 [JP] Japan .................................. 57-99565
Apr. 1, 1983 [JP] Japan .................................. 58-57060

[51] Int. Cl.$^5$ .......................................... G01N 33/546
[52] U.S. Cl. .................................... 436/533; 435/842; 436/513; 436/528; 436/531; 436/534
[58] Field of Search .................. 436/533, 534; 435/842

[56] References Cited

U.S. PATENT DOCUMENTS 3,551,555 12/1970 Schuurs ................................ 436/534
4,533,630 9/1985 Wilkins et al. ...................... 436/547

FOREIGN PATENT DOCUMENTS 0011407  3/1974  Japan .................................. 436/534
0136894 10/1979  Japan .................................. 436/533
0079956  6/1981  Japan .................................. 436/533
2027031  2/1980  United Kingdom ................ 436/533

OTHER PUBLICATIONS

Ryan, et al., Chemical Abstracts, vol. 94 (1981), 94:59144u.

Manual of Clinical Microbiology, 2nd ed. (1974), pp. 189-190.

*Primary Examiner*—Sam Rosen
*Attorney, Agent, or Firm*—Oblon, Spivak, McClelland, Maier & Neustadt

[57] ABSTRACT

Latex particles are sensitized with Immunoglobulin G obtained from the antiserum collected from a laboratory animal which has been immunized with a toxin extracted from pathogenic enterobacterium. The IgG-sensitized latex is useful for diagnosis of diseases caused by pathogenic enterobacteria.

11 Claims, No Drawings

LATEX REAGENT FOR DETECTION OF THE TOXIN OF *CLOSTRIDIUM DIFFICILE*

TECHNICAL FIELD OF THE INVENTION

This invention relates to a toxin-detecting latex reagent

BACKGROUND OF THE INVENTION

As a result of increased clinical use of varieties of antibiotic chemotherapeutic agents in recent years, symptoms primarily comprising diarrhea are today being reported in large numbers.

Such diarrheal symptoms are typically caused by pseudomembranous colitis. Virus theories, allergy theories, etc. have been propounded as the mechanism of occurrence of grave colitis of this type. However, as a result of the study on enterotoxin, an exotoxin produced by enterobacteria, it has recently come to be thought that the principle cause of such colitis is the proliferation of a certain toxogenic bacteria induced by the change in the enteric bacterioflora caused by administration of chemotherapeutic agents.

For instance, a study by Ueno et al on D-1 toxin and D-2 toxin, both of which are produced by *Clostridium difficile*, a common anaerobic enterobacterium, was published in Biochemistry International, Vol. 2, No.6, pp. 629-635, 1981. According to this report, D-1 and D-2 impair permeability of cells, injure HeLa cells and are a direct cause of pseudomembranous colitis.

Clinically, pseudomembranous colitis causes prolonged symptom of watery diarrhea containing mucus, inviting general hyposthenia, sometimes resulting in death.

In the clinical diagnosis of this disease, an S-shape colonoscope is used, biopsy of the rectum is carried out, and detection of pathogenic bacteria from feces is required. These diagnostic tests require sophisticated techniques and consume much time.

We pursued an extensive study to find ways for diagnosing pseudomembranous colitis more simply and quickly with higher accuracy. As a result of this study, we achieved this invention.

Disclosure of the Invention

This invention provides a toxin-detecting latex reagent comprising a latex the particles of which are sensitized with immunoglobulin G (IgG) which has been obtained from an antiserum against a toxin of an enterobacterium.

The toxins to be detected by the reagent of this invention include toxins produced by *Clostridium difficile, Clostridium perfrigens, Vibrio cholerae, Shigella dysenterieae, Escherichia coli, enteritis Vibrio*, etc.

The method for obtaining the antisera against these enterobacterium toxins is explained with respect to *Clostridium difficile* as an example in the following.

D-1 and D-2 toxins are obtained by the method of Ueno et al as described in the above-cited Biochemistry International.

Strains of *Clostridium difficile*, an anaerobic bacterium, are collected from feces of a pseudomembranous colitis patient and are anaerobically cultured in a culture medium containing 5% brain-heart infusion and 1% protease-pepton so as to produce D-1 and D-2 toxins. The medium is incubated at 37° C. for 48 hours and thereafter, centrifuged at 8,000 xG for 30 minutes. The supernatant is filtered with a membrane filter with 0.45 $\mu$m pores.

To the filtrate, mercaptoethanol is added so that the concentration thereof is 5 mM and the toxins are concentrated by salting out with ammonium sulfate, which is added so that the concentration thereof is 70% of saturation. The concentrated toxins are purified by chromatography with a column of AcA (an adsorbent, product of LKB, Inc.), and pure D-1 (estimated molecular weight 600,000) and D-2 (estimated molecular weight 48,000) are obtained.

Of course, only one of D-1 and D-2 can be separated and used as the starting material for preparation of the antiserum, which is explained below.

Laboratory animals (rabbit, guinea-pig, goat, etc.) are immunized with the toxins per se or the toxins detoxicated with formaldehyde, glutoraldehyde, etc., for instance, and an antiserum which has high specificity against D-1 and D-2 toxins is obtained. The antibody values of this antiserum can be confirmed by the Ouchterlony test (diffusion test in two dimensions), electrophoresis, etc.

An immunoglobulin fraction containing IgG (referred to as "IgG fraction" hereinafter) is collected from the antiserum. The method for obtaining this fraction from the obtained antiserum includes salting-out from an ammonium sulfate solution (when collection of a fraction containing IgG is intended), or fractionation of IgG with a weakly acidic ion exchange resin (when collection of a fraction containing IgG only is intended).

The thus obtained IgG fraction is dissolved in a buffer solution and vigorously agitated together with latex particles to sensitize the latex particles with IgG. The usable latexes include those of organic macromolecular substances such as polystyrene, styrene-butadiene copolymer, poly(acrylic ester), poly(methacrylic ester), etc. These latexes are well known and commercially available.

Further, the desired sensitized latexes can be obtained by chemically combining carboxylic acid-, amine-and amide-type latexes containing functional substituents with the IgG.

The thus obtained sensitized latex reagent (a suspension) of this invention can be treated with a protein solution in order to improve the storage stability and accuracy in detection of toxins. Proteins soluble in water and a buffer solution can be used for this purpose without restriction, although proteins such as albumin, globulin, fibrinogen, etc. are usually used for this purpose, and synthesized polypeptides can also be used. The concentration of the protein solution used is usually 0.01%-2%, preferably 0.1-0.5%, the pH of the solution is 5 - 10, preferably around 8. The buffer solution usually used is phosphoric acid type buffer or boric acid type buffer. The treatment is usually carried out at room temperature.

The treatment with a protein solution is, for instance, conducted as follows. The sensitized latex solution as described above is centrifuged and the supernatant is removed. The obtained precipitate is agitated with the above-mentioned protein solution for several minutes to several hours. The suspension is further centrifuged and the supernatant is removed. The collected precipitate is suspended in water or a buffer solution and thus the intended latex reagent is obtained.

The latex reagent may contain additives such as stabilizing agents, antiseptics, chelating agents, surfactants, etc. Usable buffering agents include glycine buffer, phosphoric acid buffer, citric acid buffer, barbital buffer, boric acid buffer, tris-[tris(hydroxymethy)-aminomethane]-HCl buffer, tris-malate buffer, ammonia buffer, etc.

The method for detecting toxins produced by *Clostridium difficile* in feces using the thus obtained latex reagent is as follows.

Watery or hard feces collected from a pseudomembranous colitis patient is extracted with a 0.9% NaCl solution or a phosphoric acid buffer solution containing 0.9% NaCl, and the extract is subjected to a clinical test.

When the above described latex reagent is added to the extract, coagulation of the latex occurs by the polygenic antigen-antibody reaction of the IgG on the surface of the latex particles and D-1 and D-2 toxins in the extract. The degree of coagulation of the latex is observed macroscopically on a slide glass and detection of toxins of colitis patients can be semi-quantitatively conducted. Diagnosis of pseudomembranous colitis from *Clostridium difficile* can be carried out far more rapidly with higher accuracy than the conventional methods.

If the above described latex reagent is used with an automated immunity diagnosis apparatus, a further rapid quantitative determination is possible.

DESCRIPTION OF THE PREFERRED EMBODIMENTS

The invention is now explained by way of working examples.

Example 1

D-1 and D-2 toxins which had been collected and purified by the method of Ueno et al (Biochemistry International, Vol 2, No. 6, pp. 629–635, (1981)) were treated with a 0.4% formaldehyde solution at 37° C. for 72 hours for detoxication. The detoxicated toxins were prepared into about 500 $\mu$g/ml of a solution in the physiological salt solution. The solution was well admixed with Freund's complete adjuvant (product of Difico) until the mixture became viscous. This toxin preparation was administered to a rabbit. After the first administration, the rabbit was further immunized every other week four times in all. Two weeks after the last immunization, blood was collected from the rabbit and an antiserum was obtained. The antibody value was determined by the Ouchterlony test and immunity electrophoresis. Preparation of latex reagent The obtained antiserum was prepared into a 38% ammonium sulfate solution, and the formed precipitate (a fraction containing IgG, i.e., $\gamma$-globulin) was collected. This fraction was partially purified by dialysis and used for preparation of the latex reagent. That is, the IgG fraction, which was deposited from the antiserum against D-1 and D-2 by salting out with ammonium sulfate (38% of saturation) was dissolved in an 0.2 M boric acid solution (pH 8.0) so that the concentration was 800–1500 antibodies per one particle of the latex to be used. A latex-boric acid buffer solution (pH 8) was prepared using a polystyrene latex having particle diameter of 0.48 $\mu$m (product of Dow Chemical Corp.) and a boric acid buffer solution. The above-mentioned IgG solution was mixed with an equal amount of said latex-boric acid buffer solution and well agitated so as to cause satisfactory sensitization. The mixture was centrifuged and the supernatant was removed. The thus obtained precipitate was treated with the boric acid buffer solution containing 0.2% bovine serum albumin at room temperature for 15 minutes under agitation. The mixture was further centrifuged and the supernatant was removed and the obtained latex particles were suspended in a boric acid buffer solution for use. This latex reagent was stable for not less than 6 months and retained stable accuracy in clinical tests.

Example 2

Feces of a colitis patient was added to a 10% physiological salt solution and was vigorously agitated. The mixture was centrifuged at 3,000 rpm for 10 minutes and the supernatant was collected and filtered with a 0.45 $\mu$m millipore filter. The filtrate was used as a sample.

One hundred (100) $\mu$l physiological salt solution containing 0.2% bovine serum albumin was dropped on a slide glass, and 50 $\mu$l of the above described sample solution was added thereto. After the above two were well mixed, 30 $\mu$l of the latex reagent was added and mixed. After a few minutes, formation of latex clots was macroscopically observed.

When the extract of feces of a normal person was used as the sample, the latex particles remained in the state of suspension and no coagulation thereof was observed. In contrast, the sample from feces of a pseudomembranous colitis patient caused distinct coagulation of latex particles and the degree of the coagulation was proportional to the concentration of the toxins.

Example 3

The same clinical sample solution as used in Example 2 was used for the test by means of an optical immunological diagnosis system ("LPIA (Latex Photometric Immunoassay)" manufactured by Mistubishi Chemical Industries Ltd.). Fifty (50) $\mu$l of the sample solution was taken into a reaction cuvette and 200 $\mu$l of a buffer solution containing 0.1% bovine serum albumin was added thereto to make 250 $\mu$l. Fifty (50) $\mu$l of the latex reagent (1% latex solution) prepared in Example 1 was automatically fed in the reaction cuvette together with 200 $\mu$l of a physiological salt solution containing 0.1% bovine serum albumin. Thus change in turbidity due to the antigen-antibody reaction in the latex reaction mixture (500 $\mu$l in total). Reaction was monitored for 60 seconds at 940 nm wave length. A calibration curve concerning the degree of the change with respect to the standard samples had been prepared. The amount of the toxins of *Clostridium difficile* in the sample was accurately determined.

Although the invention has been described in detail with respect to a few specific examples pertaining to *Clostridium difficile*, those skilled in the art who read the description will understand that latex reagents for detecting toxins of enterobacteria other than *Clostridium difficile* can be obtained in accordance with the knowledge of clinical biochemistry.

We claim:

1. A latex reagent for the detection of the toxin of *Clostridium difficile*, comprising:
   a latex of particles sensitized with Immunoglobulin G (IgG) which has been obtained from an antiserum, said antiserum being obtained from an animal immunized against the toxins of *Clostridium difficile*.

2. The toxin-detecting latex reagent as recited in claim 1, wherein the latex particles sensitized with IgG are treated with a protein solution.

3. The toxin-detecting latex reagent as recited in claim 2, wherein the latex particles sensitized with IgG are treated with a solution of a protein selected from the group consisting of albumin, globulin and fibrinogen.

4. The toxin-detecting latex reagent as recited in claim 1, wherein the latex is a member selected from the group consisting of polystyrene latex, styrene-butadiene copolymer latex, poly(acrylic acid ester) latex, and poly(methacrylic acid ester) latex.

5. A process for preparing a latex reagent for the detection of toxins of *Clostridium difficile*:
   (a) collecting an antiserum effective against toxin of *Clostridium difficile*;
   (b) collecting an IgG containing fraction therefrom; and
   (c) sensitizing latex particles with said IgG fraction.

6. The process for preparing the toxin-detecting latex reagent as recited in claim 5 wherein the latex particles sensitized with IgG are treated with a protein solution.

7. The process for preparing the toxin-detecting latex reagent as recited in claim 5, wherein the latex is member selected from the group consisting of polystyrene latex, styrene-butadiene copolymer latex, poly(acrylic acid ester) latex, and poly(methacrylic acid ester) latex.

8. The process for preparing the toxin-detecting latex reagent as recited in claim 6, wherein the latex solution sensitized with IgG is treated with a solution of a protein selected from the group consisting of albumin, globulin and fibrinogen.

9. The toxin-detecting latex reagent as recited in claim 2, wherein the concentration of said protein solution in said latex reagent ranges from 0.01%-2%.

10. The toxin-detecting latex reagent as recited in claim 2, wherein the pH of said protein solution ranges from 5-10.

11. A method for conducting an assay to determine the presence of a toxin of *C. difficile* in a specimen, comprising:
   contacting said specimen with the latex reagent of claim 1, and determining the presence of absence of agglutination.

* * * * *